United States Patent
Ellis et al.

(10) Patent No.: US 7,553,943 B2
(45) Date of Patent: Jun. 30, 2009

(54) POLYNUCLEOTIDE ARRAYS

(75) Inventors: Darren James Ellis, Waldon (GB);
Colin Lloyd Barnes, Waldon (GB);
Harold Philip Swerdlow, Waldon (GB);
Tom Brown, Highfield (GB)

(73) Assignee: Illumina Cambridge Limited, Nr. Saffron Walden (GB)

( * ) Notice: Subject to any disclaimer, the term of this patent is extended or adjusted under 35 U.S.C. 154(b) by 62 days.

(21) Appl. No.: 10/578,460

(22) PCT Filed: Nov. 8, 2004

(86) PCT No.: PCT/GB2004/004707

§ 371 (c)(1),
(2), (4) Date: Feb. 22, 2007

(87) PCT Pub. No.: WO2005/047301

PCT Pub. Date: May 26, 2005

(65) Prior Publication Data

US 2007/0269806 A1    Nov. 22, 2007

(30) Foreign Application Priority Data

Nov. 7, 2003    (GB) .................................. 0326073.4

(51) Int. Cl.
C07H 21/00    (2006.01)
C07H 21/02    (2006.01)
C07H 21/04    (2006.01)
C12Q 1/68     (2006.01)
C12P 19/34    (2006.01)

(52) U.S. Cl. .................. 536/23.1; 536/24.3; 536/24.33; 536/25.3; 435/6; 435/91.1

(58) Field of Classification Search ................ 536/23.1, 536/24.3, 24.33, 25.3; 435/6, 91.1
See application file for complete search history.

(56) References Cited

U.S. PATENT DOCUMENTS

| 4,659,774 A | 4/1987 | Webb et al. |
| 2003/0022207 A1 | 1/2003 | Balasubramanian et al. |

FOREIGN PATENT DOCUMENTS

| EP | 0 174 879 B1 | 3/1986 |
| WO | WO 97/08183 | 3/1997 |
| WO | WO 00/53616 | 9/2000 |
| WO | WO 01/16152 | 3/2001 |
| WO | WO 01/92284 A1 | 12/2001 |
| WO | WO 02/061126 | 8/2002 |

OTHER PUBLICATIONS

Zhao et al., Immobilization of oligodeoxyribonucleotides with multiple anchors to microchips, Nucleic Acids Research, 29:955-959 (2001).

(Continued)

*Primary Examiner*—Jezia Riley
(74) *Attorney, Agent, or Firm*—Klauber & Jackson LLC

(57) ABSTRACT

The invention provides a hairpin polynucleotide, having a loop and a stem region, characterised in that a sulfur-based nucleophile is attached to an internal nucleotide in the hairpin through a linker to enable binding to a solid support.

36 Claims, 3 Drawing Sheets

1

3

2

4

OTHER PUBLICATIONS

Broude, Stem-loop oligonucleotides: a robust tool for molecular biology and biotechnology, Trends in Biotechnology, 20:249-256 (2002).

Fang et al., Designing a Novel Molecular Beacon for Surface-Immobilized DNA Hybridization Studies, J. Am. Chem. Soc., 121:2921-2922 (1999).

Pirrung et al., Novel Reagents and Procedures for Immobilization of DNA on Glass Microchips for Primer Extension, Langmuir; 16:2185-2191 (2000).

Riccelli et al., Hybridzation of single-stranded DNA targets to immobilized complementary DNA probes: comparison of hairpin versus linear capture probes, Nucleic Acids Research, 29:996-1004 (2001).

D E

POLYNUCLEOTIDE ARRAYS

CROSS REFERENCE TO RELATED APPLICATIONS

The present application is a National Stage Application claiming the priority of co-pending PCT Application No. PCT/GB2004/004707 filed Nov. 8, 2004, which in turn, claims priority from Great Britain Application Serial No. 0326073.4, filed Nov. 7, 2003. Applicants claim the benefits of 35 U.S.C. § 120 as to the PCT application and priority under 35 U.S.C. § 119 as to the said Great Britain application, and the entire disclosures of both applications are incorporated herein by reference in their entireties.

FIELD OF THE INVENTION

This invention relates to the construction of arrays of polynucleotides. In particular, the invention relates to the preparation, and use in the formation and manipulation of arrays, of polynucleotides having a hairpin structure.

BACKGROUND

Advances in the study of molecules have been led, in part, by improvement in technologies used to characterise the molecules or their biological reactions. In particular, the study of nucleic acids, such as DNA and RNA, and other large biological molecules, such as proteins, has benefited from developing technologies used for sequence analysis and the study of hybridisation events.

An example of the technologies that have improved the study of nucleic acids is the development of fabricated arrays of immobilised nucleic acids. These arrays typically consist of a high-density matrix of polynucleotides immobilised onto a solid support material. Fodor et al., *Trends in Biotechnology* (1994) 12:19-26, describe ways of assembling the nucleic acid arrays using a chemically sensitised glass surface protected by a mask, but exposed at defined areas to allow attachment of suitably modified nucleotides. Typically, these arrays may be described as "many molecule" arrays, as distinct regions are formed on the solid support comprising a high density of one specific type of polynucleotide.

An alternative approach is described by Schena et al., *Science* (1995) 270:467-470, where samples of DNA are positioned at predetermined sites on a glass microscope slide by robotic micropipetting techniques.

A further development in array technology is the attachment of the polynucleotides to a solid support material to form single molecule arrays (SMAs). Arrays of this type are disclosed in WO00/06770. The advantage of these arrays is that reactions can be monitored at the single molecule level and information on large numbers of single molecules can be collated from a single reaction.

Although these arrays offer particular advantages in sequencing experiments, the preparation of arrays at the single molecule level is more difficult than at the multi-molecule level, where losses of target polynucleotide can be tolerated due to the multiplicity of the array. There is, therefore, a constant need for improvements in the preparation of single molecule arrays for sequencing procedures. In particular, it is desirable to be able to attach sample polynucleotide (e.g. DNA) from solution under conditions which minimise the non-specific association of sample polynucleotide (e.g. DNA) to the solid support.

Sequencing polynucleotides on a solid support can be difficult because the polynucleotide to be sequenced is typically bound to the solid support indirectly by way of the formation of a hybrid with a support-bound complement. Conditions used in the sequencing protocol can result in disruption to the bonds formed on hybridisation and the target polynucleotide may be removed from the array. By "target polynucleotides" or "target nucleic acid" is meant herein the polynucleotide whose sequence it is desired to determine.

Accordingly, research has been directed to develop sequencing methodologies where the target nucleic acid is bound to a solid support and which address the disruption of polynucleotide duplexes caused by the lability of the hydrogen bonds formed between complementary nucleotide bases. Such techniques have led to the development and use of polynucleotides having hairpin stem-loop structure, referred to hereinafter as hairpin polynucleotides.

The term "hairpin loop structure" refers to a molecular stem and loop formed from the hybridisation of complementary polynucleotides that are covalently linked at one end. The stem comprises the hybridised polynucleotides and the loop is the region that links the two complementary polynucleotides.

WO98/20019 discloses compositions and methods for the preparation of nucleic acid arrays. The general disclosure relates to the preparation of high density multi-molecule arrays, achieved by immobilising polynucleotides on microscopic beads attached to a solid support. Many different uses are proposed for the arrays.

WO97/08183 relates to nucleic acid capture molecules. Hairpin polynucleotide structures are disclosed as being useful as capture molecules in hybridisation-based nucleic acid detection methods.

Hairpin polynucleotides permit improved sequence analysis procedures to be conducted, since a target polynucleotide may be maintained in spatial relationship to a primer. Maintenance of the spatial relationship is made possible not only by the hydrogen bonds formed on hybridisation, but also by the tethering of a known primer to the target polynucleotide, the tether being the "loop" (see WO97/04131).

In WO97/04131, the hairpin is immobilised on a glass support by reaction between a pendant epoxide group on the glass with an internal amino group held within the loop. This method of immobilising hairpin polynucleotides on solid supports is but one of a number of linking methodologies which have been developed to date.

Zhao et al (Nucleic Acids Research, 2001, 29(4), 955-959) disclose the formation of a hairpin polynucleotide which contains multiple phosphorothioate moieties in the loop. The moieties are used to anchor, in more than one position, the hairpin DNA to glass slides pre-activated with bromoacetamidopropylsilane. This chemistry was found to improve attachment of hairpin DNA to glass slides.

The work of Zhao developed upon earlier work of Pirrung et al (*Langmuir,* 2000, 16, 2185-2191) in which the authors report that 5'-thiophosphate-terminating oligonucleotides could be attached to glass, pre-activated with mono- and dialkoxylated silanes and bromoacetamide.

Phosphorothioate coupling chemistry works well where the solution applied is dried down onto the support. However, the conditions under which phosphorothioate coupling is effected are not applicable in to the preparation of SMAs. This is because when drying down the applied solution in the protocol used for phosphorothioate coupling, this may take place non-uniformly. This is the case when oligonucleotides are spotted onto preactivated glass, for example as taught by Zhao (infra) where small volumes (0.7 nl) are used. Accordingly, clustering can take place on the surface of the support which is clearly undesirable in the preparation of a SMA.

SUMMARY OF THE INVENTION

The present invention is based on the surprising finding that when hairpin polynucleotides are attached to a solid support, e.g. for use in the preparation of SMAs, by reaction of a sulfur-based nucleophile with the solid support, improved adhesion to the solid support is effected as compared to attachment through backbone phosphorothioate moieties. The sulfur-based nucleophile may be directly attached to the hairpin although it is preferably indirectly attached through a linker. Attachment is by way of an internal nucleotide within the hairpin, that is to say that the sulfur-based nucleophile is not connected directly or through a linker to a nucleotide at either terminus of the hairpin.

Viewed from a first aspect, therefore, the invention provides a hairpin polynucleotide, having a loop and a stem region,.characterised in that a sulfur-based nucleophile is attached to an internal nucleotide in the hairpin through a linker to enable binding to a solid support.

In another aspect, the invention provides a method of making a hairpin polynucleotide, having a loop and a stem region, having a sulfur-based nucleophile attached to an internal nucleotide in the hairpin through a linker to enable binding to a solid support, which method comprises incorporating the sulfur-based nucleophile into said internal nucleotide before, after or during formation of the hairpin polynucleotide, particularly before or during formation.

In a further aspect, the invention provides an array of hairpin polynucleotides as described herein immobilised on a surface of a solid support by reaction between the sulfur-based nucleophile and the surface of the solid support.

In an even further aspect, the invention provides a method of making an array of hairpin polynucleotides, having a loop and a stem region, comprising the steps of:

(i) preparing a plurality of hairpin polynucleotides as described herein; and (ii) immobilising said hairpin polynucleotides on a surface of a solid support so as to form said array.

Additionally, in another aspect, the invention provides a device comprising an array of hairpin polynucleotides as described herein.

The invention also provides the use of such a device in the interrogation of said polynucleotides comprising an array of hairpin polynucleotides.

DETAILED DESCRIPTION

Figure 1:
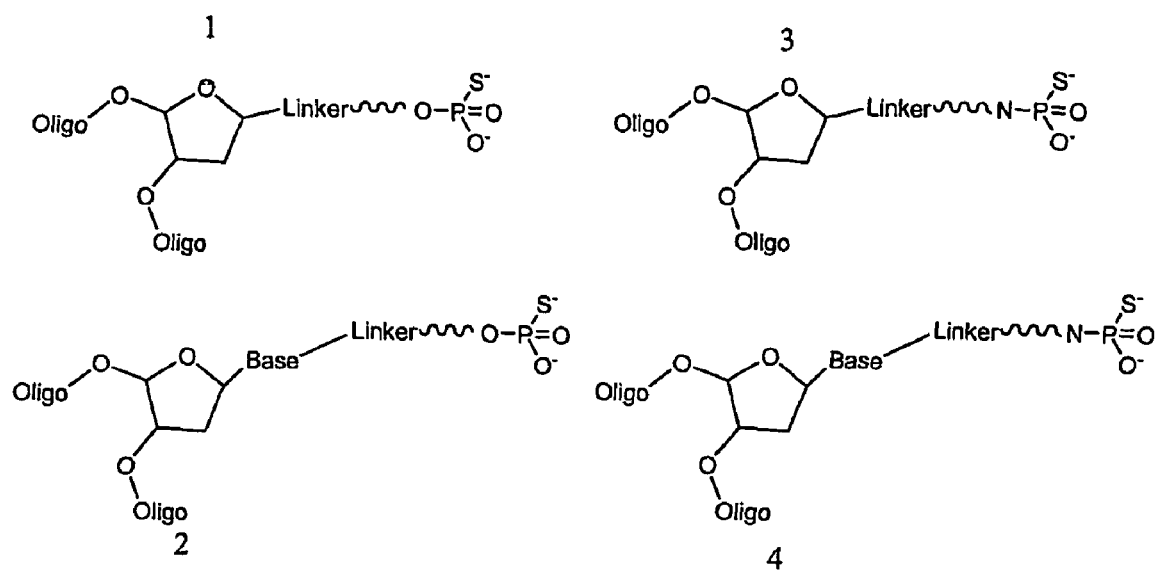
FIG. 1 shows, schematically, exemplary structures of portions of hairpin polynucleotides according to the invention in which the terminal sulfur-based nucleophile shown (either a thiophosphate or a thiophosphoramidate) is attached through a linker either to the base of a nucleotide or the sugar of an a basic nucleotide.

As used herein, the term 'polynucleotide' refers to nucleic acids in general, including DNA (e.g. cDNA), RNA (e.g. mRNA) and synthetic analogs, e.g. PNA or 2'-O-methyl-RNA. DNA is preferred.

The term SMA as used herein refers to a population of polynucleotide molecules, distributed (or arrayed) over a solid support, wherein the spacing of any individual polynucleotide from all others of the population is such that it is possible to effect individual resolution, or interrogation, of the polynucleotides.

As discussed in part earlier, the polynucleotides of the invention are of hairpin loop structure. Anything from a 5 to 25 (or more) base pair double-stranded (duplex) region may be used to form the stem.

In one embodiment, the stem structure may be formed from a single-stranded polynucleotide having complementary regions. The loop in this embodiment may be anything from 2 or more non-hybridised nucleotides. In a second embodiment, the structure may be formed from two separate polynucleotides with complementary regions, the two polynucleotides being connected (and the loop being formed) by a connecting moiety. The connecting moiety forms a covalent attachment between the ends of the two polynucleotides. Connecting moieties suitable for use in this embodiment will be apparent to the skilled person. For example, the connecting moiety may comprise polyethylene glycol (PEG).

Those skilled in the art will appreciate that the loop may alternatively comprise a combination of non-hybridised polynucleotide moieties and suitable connecting moieties. Thus, as an example, a loop could be formed from a modified nucleotide residue (e.g. an abasic nucleotide) flanked by regions of PEG, for example, by two 18-atom hexaethylene glycol (heg) spacers.

The hairpin polynucleotides of the invention are characterised in that a sulfur-based nucleophile is neither attached to the phosphate backbone between adjacent nucleotides nor the terminal positions of the hairpin nucleotide hairpin. Preferably attachment is at one or more positions in the loop region of the hairpin.

It is within the scope of this invention for each hairpin polynucleotide to contain more than one sulfur-based nucleophile all or some of which, preferably all of which, are attached through a linker to the hairpin polynucleotide. Most preferably, each hairpin polynucleotide contains only one sulfur-based nucleophile, preferably a thiophosphate.

The sulfur-based nucleophiles which, in part, characterise the various aspect of this invention are not particularly restricted. The sulfur-based nucleophile may thus be a simple thiol (~SH wherein~denotes the bond or linker connecting the thiol to the remainder of the polynucleotide). Further examples of sulfur-based nucleophiles include a moiety of the formula (I):

(I)

(wherein ~ denotes the bond or linker connecting the sulfur-based nucleophile to the remainder of the polynucleotide; X represents an oxygen atom, a sulfur atom or a group NR, in which R is hydrogen or an optionally substituted $C_{1-10}$ alkyl; Y represents an oxygen or a sulfur atom; and Z represents an oxygen atom, a sulfur atom or an optionally substituted $C_{1-10}$ alkyl group).

Preferred moieties of formula (I) are those in which X is oxygen or sulfur, preferably oxygen. Where X is a group NR, R is preferably hydrogen. Y is preferably oxygen. Z is preferably an oxygen or sulfur atom or a methyl group, particularly preferably an oxygen atom.

In all aspects of the invention, the preferred sulfur-based nucleophile is thiophosphate although it is to be understood that the invention is not so limited since the other sulfur-based nucleophiles described are also of utility, for example thiophosphoramidates.

Where alkyl (including cycloalkyl) groups are substituted, examples of appropriate substituents include halogen substituents or functional groups such as hydroxyl, amino, cyano, nitro, carboxyl and the like.

The linker molecule can be any moiety that results in a sulfur-based nucleophile, e.g. a primary thiophosphate. An example of how this might be achieved is by the presence of a modified nucleotide such as an abasic nucleotide, preferably in the loop. In an abasic nucleotide, a sulfur-based nucleophile may be attached to the 1'-carbon atom of the ribose (in place of the missing base). Alternatively, the sulfur-based nucleophile may be attached to the base of a nucleotide.

Examples of each of these are shown schematically in FIG. 1 in which structures 1 and 3 show the attachment of terminal sulfur-based nucleophiles through linkers to abasic nucleotides attached to the rest of the hairpin (indicated as "Oligo"), and structures 2 and 4 show attachment of sulfur-based nucleophile through linkers attached to bases.

Particularly preferred hairpin nucleotides according to this invention are those in which the loop comprises non-hybridised nucleotides and the sulfur-based nucleophile is attached to such nucleotides through a linker moiety. Appropriate nucleotides in such embodiments include modified nucleotides in which the linker attached to the base of the nucleotide. The base may be any base present in nucleotides but will typically be one of the four major bases: adenine, guanine, cytosine and uracil, particularly uracil.

Generally, a linker is present in the hairpin nucleotides of the invention. The linker may be a carbon-containing chain such as those of formula $(CH_2)_n$ wherein "n" is from 1 to about 1500, for example less than about 1000, preferably less than 100, e.g. from 2-50, particularly 5-25. However, a variety of other linkers may be employed with the only restriction placed on their structures being that the linkers are stable under conditions used in DNA sequencing.

Linkers which do not consist only of carbon atoms may be used. Such linkers include polyethylene glycol (PEG) having general formula $(CH_2—CH_2—O)_m$ wherein m is from about 1 to 600, preferably less than about 500.

Linkers formed primarily from chains of carbon atoms and from PEG may be modified so as to contain functional groups which interrupt the chains. Examples of such groups include ketones, esters, amines, amides, ethers, thioethers, sulfoxides, sulfones. Separately or in combination with the presence of such functional groups may be employed alkene, alkyne, aromatic or heteroaromatic moieties, or cyclic aliphatic moieties (e.g. cyclohexyl). Cyclohexyl or phenyl rings may, for example, be connected to a PEG or $(CH_2)_n$ chain through their 1- and 4-positions.

Examples of appropriately modified linkers are those of formula $(CH_2)_n$ (wherein n is as defined above) and in which one or more $CH_2$ units are replaced with functional groups). Thus, one or more $CH_2$ units may be exchanged for an oxygen to form an ether, or for a $SO_2$ to form a sulfone etc. One or more $CH_2$ units may be exchanged for an amide moiety or alkene or alkyne unit. In such linkers one or more functional groups may be present; these functional groups may or may not be the same as each other.

Linkers of particular interest contain the propargylamino unit attached to the base (e.g. uracil) in a modified nucleotide. Such nucleotides contain the following unit:

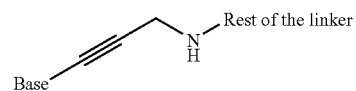

The amino group may be connected to the remainder of the linker by formation of an amide bond.

Modified nucleotides are commercially available, e.g. from the DNA synthesis company Oswel. Such nucleotides include 3'OH capped nucleotides which may be abasic where a capped linker is attached at the 1'carbon atom or contain a base to which a capped linker is attached. Two such modified nucleotides are Oswel products OSW428 and OSW421:

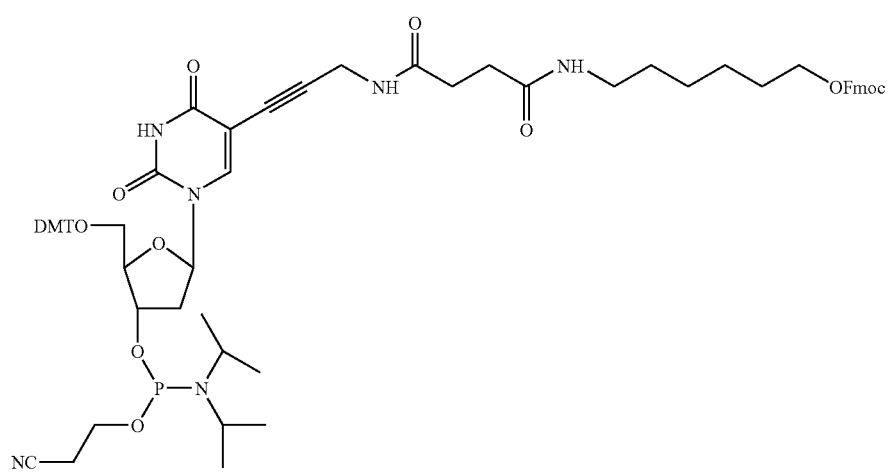

OSW428

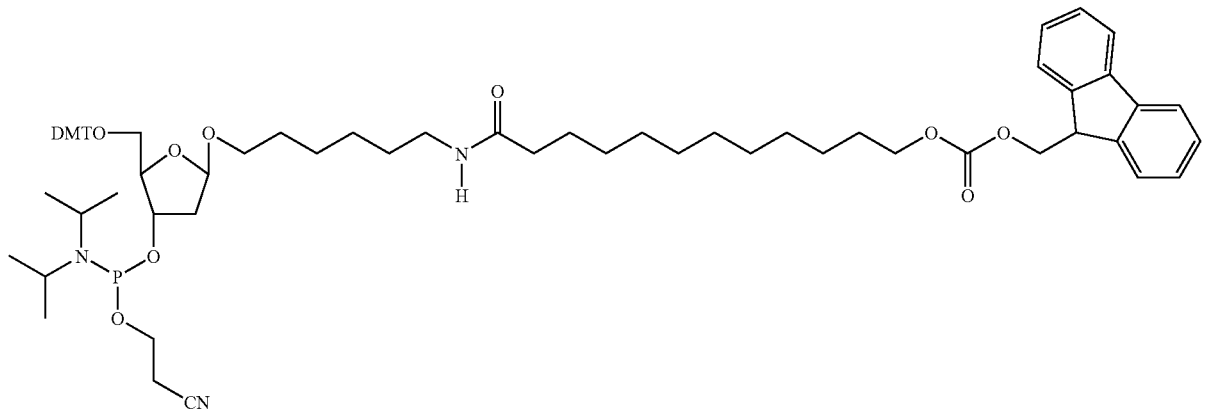

OSW421

Those skilled in the art will be aware how to deprotect the fluorenylmethoxycarbonyl (Fmoc) group shown capping the linker in the nucleotides shown above and to effect terminal modification, e.g. thiophosphorylation, of the linker.

As an alternative to the linkers described above, which are primarily based on linear chains of saturated carbon atoms, optionally interrupted with unsaturated carbon atoms or heteroatoms other linkers may be envisaged which are based on nucleic acids or monosaccharide units (e.g. dextrose). It is also within the scope of this invention to utilise peptides as linkers.

Longer linker moieties serve (e.g. those containing a chain or more than 100 atoms, particularly those in excess of 500 or even 1000 atoms) serve to position the oligonucleotide further away from the solid support. This places the oligonucleotide (e.g. DNA) in a environment more resembling free solution which can be beneficial, for example, in any enzyme-mediated reactions effected to the oligonucleotide. This is because such reactions suffer less from the steric hindrance which manifests itself where the oligonucleotide is directly attached to the support or is indirectly attached through a very short linker (such as one comprising a chain or only several, e.g. about 1 to 3 carbon atoms).

As is known, by incorporating the means of attaching the hairpin polynucleotide to a support internally, this leaves both the 3' and 5' ends of the polynucleotide free for use in subsequent interrogations either before or after binding of the hairpin polynucleotide to the support.

The hairpin polynucleotides in addition to a sulfur-based nucleophile preferably comprise a polynucleotide duplex which may be used to retain a primer and a target polynucleotide in spatial relationship. Preferably the target polynucleotide is present at the 5' end and the primer is present at the 3' end although hairpin polynucleotides where the primer is present at the 5' end and the target polynucleotide is present at the 3' end are also embraced by this invention.

As used herein, the term "interrogate" refers to the target polynucleotide functioning as a template upon which DNA polymerase acts. In other words, "interrogating" means contacting the target polynucleotides with another molecule, e.g., a polymerase, a nucleoside triphosphate, a complementary nucleic acid sequence, wherein the physical interaction provides information regarding a characteristic of the arrayed target polynucleotide. The contacting can involve covalent or non-covalent interactions with the other molecule. As used herein, "information regarding a characteristic" means information about the sequence of one or more nucleotides in the target polynucleotide, the length of the polynucleotide, the base composition of the polynucleotide, the $T_m$ of the polynucleotide, the presence of a specific binding site for a polypeptide or other molecule, the presence of an adduct or modified nucleotide, or the three-dimensional structure of the polynucleotide.

The spatial relationship between primer and target polynucleotide present in hairpin polynucleotides permits improved sequence analysis procedures to be conducted. Maintenance of the spatial relationship is made possible not only by the hydrogen bonds formed on hybridisation, but also by the tethering of a known primer to the target polynucleotide. The fixing of the primer, as part of the hairpin structure, to the solid support, ensures that the primer is able to perform its priming function during a polymerase-based sequencing procedure, and is not removed during any washing step in the procedure.

There are many different ways of forming the hairpin structure so as to incorporate the target polynucleotide. A preferred method is to form a first molecule (which may contain a non-backbone sulfur-based nucleophile attached through a linker) capable of forming a hairpin structure, and ligate the target polynucleotide to this. It is possible to ligate any desired target polynucleotide to the hairpin construct before or after arraying the hairpins on the solid support. Alternatively, a first polynucleotide may be ligated before arraying and a second ligated after arraying. It is, of course, also possible to introduce the sulfur-based nucleophile after such a ligation.

Where a target polynucleotide is a double-stranded DNA, this may be attached to the stem of the hairpin by ligating one strand to the hairpin polynucleotide and removing the other strand after the ligation.

In one embodiment, the target polynucleotide is genomic DNA purified using conventional methods. The genomic DNA may be PCR-amplified or used directly to generate fragments of DNA using either restriction endonucleases, other suitable enzymes, a mechanical form of fragmentation or a non-enzymatic chemical fragmentation method. In the case of fragments generated by restriction endonucleases, hairpin structures bearing a complementary restriction site at the end of the first hairpin may be used, and selective ligation of one strand of the DNA sample fragments may be achieved by one of two methods.

Method 1 uses a hairpin containing a phosphorylated 5' end. Using this method, it may be necessary to first de-phosphorylate the restriction-cleaved genomic or other DNA fragments prior to ligation such that only one sample strand is covalently ligated to the hairpin.

Method 2: in the design of the hairpin, a single (or more) base gap can be incorporated at the 3' end (the receded strand) such that upon ligation of the DNA fragments only one strand is covalently joined to the hairpin. The base gap can be formed by hybridising a further separate polynucleotide to the 5'-end of the first hairpin structure. On ligation, the DNA fragment has one strand joined to the 5'-end of the first hairpin, and the other strand joined to the 3'-end of the further polynucleotide. The further polynucleotide (and the other stand of the fragment) may then be removed by disrupting hybridisation.

In either case, the net result should be covalent ligation of only one strand of a DNA fragment of genomic or other DNA to the hairpin. Such ligation reactions may be carried out in solution at optimised concentrations based on conventional ligation chemistry, for example, carried out by DNA ligases or non-enzymatic chemical ligation. Should the fragmented DNA be generated by random shearing of genomic DNA or polymerase, then the ends can be filled in with Klenow fragment to generate blunt-ended fragments which may be blunt-end-ligated onto blunt-ended hairpins. Alternatively, the blunt-ended DNA fragments may be ligated to oligonucleotide adapters which are designed to allow compatible ligation with the sticky-end hairpins, in the manner described previously.

Once formed, one or a plurality of sulfur-based nucleophile-bearing hairpin polynucleotides may be bound directly or indirectly to a solid support, immobilising them through a covalent bond between each polynucleotide (by way of the sulfur-based nucleophile) and the support. In doing so it is thus possible to generate arrays, e.g. SMAs, of the hairpin polynucleotides.

The precise density of the arrays is not critical. Provided single molecule resolution may be effected, in fact, the higher the density of hairpin polynucleotide molecules arrayed the better since more information may be obtained from any one experiment. For example, there may be at least $10^3$ molecules/$cm^2$, preferably at least $10^5$ molecules/$cm^2$ and most preferably $10^6$-$10^9$ molecules/$cm^2$. Particularly preferably, the density of sample molecules is at least $10^7$/$cm^2$, typically it is approximately $10^8$-$10^9$/$cm^2$.

Such "high density" arrays are in contrast to those arrays such as those so described in the prior art which are not necessarily as high or, e.g. in the many molecule arrays of Fodor et al (infra), are too high to allow single molecule resolution. By arraying the polynucleotides at a density that they can be considered to be single molecules, i.e. each can be individually resolved, a SMA is created.

The terms "individually resolved" and "individual resolution" are used herein to specify that, when visualised, it is possible to distinguish one molecule on the array from its neighbouring molecules. Separation between individual molecules on the array will be determined, in part, by the particular technique used to resolve the individual molecules. It will usually be the target polynucleotide portion that is individually resolved, as it is this which will be interrogated, e.g. by the incorporation of detectable bases.

Bonding between support and hairpin polynucleotide may be effected once the surface of the support has been modified with an activating group so that it possesses surface functionality capable of forming a bond with the sulfur-based nucleophile, or improving the ability of the surface to do so.

There is no particular limitation placed upon the solid support to which the hairpin polynucleotides of the invention may be attached. Suitable solid supports are available commercially, and will be apparent to the skilled person. The solid support may be any of the conventional supports used in "DNA chips" and can be manufactured from materials such as glass, ceramics, silica, silicon or plastics materials. Supports with a gold surface may also be used. The supports usually comprise a flat (planar) surface, such as a glass slide, or at least a structure in which the polynucleotides to be interrogated are in approximately the same plane. Alternatively, the solid support can be non-planar, e.g., a microbead or polymeric (such as plastics) support. Any suitable size may be used. For example, the supports might be on the order of 1-10 cm in each direction. The target polynucleotide may be any nucleic acid (single- or double-stranded).

In general, the surface of the support is engineered such that it displays an electrophilic group. Thus, a first step in the fabrication of arrays of hairpin polynucleotides will usually be to functionalise the surface of the solid support, to make it suitable for attachment of the polynucleotides. For example, silicon-containing moieties have been used previously to attach molecules to a solid support material, usually a glass slide.

Appropriate surface modifications will be known to those in the art and include, for example the coating of glass with siloxanes. Particularly preferred are the monolkoxylated and dialkoxylated silanes/bromoacetamide protocol set forth by Pirrung et al (infra).

In one embodiment, the surface is modified so that it in part comprises a silane of formula $R_n SiX_{(4-n)}$ (where R is an inert moiety that is displayed on the surface of the solid support, n is an integer of from 1 to 4, preferably 3 and X is or comprises a reactive leaving group such as a halide (e.g., Cl, Br) or alkoxide (e.g. a $C_{1-6}$ alkoxide). Such modified surfaces may be created by reaction with silanes such as tetraethoxysilane, triethoxymethylsilane, diethoxydimethylsilane or glycidoxypropyltriethoxysilane, although many other suitable examples will be apparent to the skilled person. Preferred is a mixture of tetraethoxysilane and triethoxysilylpropyl(bromoacetamide). However the precise nature of the surface modification is not of particular importance to this invention so long as the surface is rendered capable of bonding to (e.g. forming a covalent bond on reaction with) the sulfur-based nucleophile in the hairpin polynucleotide.

Immobilisation of the polynucleotides to the solid support may be carried out by any method known in the art, provided that covalent attachment is achieved. Thus, the single molecule array may be prepared by contacting a suitably prepared solid support with a dilute solution containing the polynucleotides to be arrayed. Appropriate concentrations of solutions in this regard will depend upon factors such as the reaction between each individual sulfur-based nucleophile in the polynucleotide and the surface to which it is attached.

Once formed, the arrays may be used in procedures to determine the sequence of the target polynucleotide. For example, the arrays may be used to determine the properties or identities of cognate molecules. Typically, interaction of biological or chemical molecules with the arrays are carried out in solution.

In particular, the arrays may be used in conventional assays which rely on the detection of fluorescent labels to obtain information on the arrayed polynucleotides. The arrays are particularly suitable for use in multi-step assays where the loss of synchronisation in the steps was previously regarded as a limitation to the use of arrays. The arrays may be used in conventional techniques for obtaining genetic sequence information. Many of these techniques rely on the stepwise identification of suitably labelled nucleotides, referred to in U.S. Pat. No. 5,654,413 as "single base" sequencing methods.

In an embodiment of the invention, the sequence of a target polynucleotide is determined in a similar manner to that described in U.S. Pat. No. 5,654,413, by detecting the incorporation of nucleotides into the nascent strand through the detection of a fluorescent label attached to the incorporated nucleotide. The target polynucleotide is primed with a suitable primer (or prepared as a hairpin construct which will contain the primer as part of the hairpin), and the nascent chain is extended in a stepwise manner by the polymerase reaction. Each of the different nucleotides (A, T, G and C) incorporated a unique fluorophore at the 3' position which acts as a blocking group to prevent uncontrolled polymerisation. The polymerase enzyme incorporates a nucleotide into the nascent chain complementary to the target polynucleotide, and the blocking group prevents further incorporation of nucleotides. The array surface is then cleared of unincorporated nucleotides and each incorporated nucleotide is "read" optically by a charge-coupled device using laser excitation and filters. The 3'-blocking group is then removed (deprotected), to expose the nascent chain for further nucleotide incorporation.

Similarly, U.S. Pat. No. 5,302,509 discloses a method to sequence polynucleotides immobilised on a solid support. The method relies on the incorporation of fluorescently-labelled, 3'-blocked bases A, G, C and T to the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

Because the array consists of distinct optically resolvable polynucleotides, each target polynucleotide will generate a series of distinct signals as the fluorescent events are detected. Details of the full sequence are then determined.

The term "individually resolved by optical microscopy" is used herein to indicate that, when visualised, it is possible to distinguish at least one polynucleotide on the array from its neighbouring polynucleotides using optical microscopy methods available in the art. Visualisation may be effected by the use of reporter labels, e.g., fluorophores, the signal of which is individually resolved.

Other suitable sequencing procedures will be apparent to the skilled person. In particular, the sequencing method may rely on the degradation of the arrayed polynucleotides, the degradation products being characterised to determine the sequence.

An example of a suitable degradation technique is disclosed in WO95/20053, whereby bases on a polynucleotide are removed sequentially, a predetermined number at a time, through the use of labelled adaptors specific for the bases, and a defined exonuclease cleavage.

A consequence of sequencing using non-destructive methods is that it is possible to form a spatially addressable array for further characterisation studies, and therefore non-destructive sequencing may be preferred. In this context, the term "spatially addressable" is used herein to describe how different molecules may be identified on the basis of their position on an array.

In the case that the target polynucleotide fragments are generated via restriction digest of genomic DNA, the recognition sequence of the restriction or other nuclease enzyme will provide 4, 6, 8 bases or more of known sequence (dependent on the enzyme). Further sequencing of between 10 and 20 bases on the SMA should provide sufficient overall sequence information to place that stretch of DNA into unique context with a total human genome sequence, thus enabling the sequence information to be used for genotyping and more specifically single nucleotide polymorphism (SNP) scoring.

The sequencing method that is used to characterise the bound target may be any known in the art that measures the sequential incorporation of bases onto an extending strand. A suitable technique is disclosed in U.S. Pat. No. 5,302,509 requiring the monitoring of sequential incorporation of fluorescently-labelled bases onto a complement using the polymerase reaction. Alternatives will be apparent to the skilled person. Suitable reagents, including fluorescently-labelled nucleotides will be apparent to the skilled person.

Thus the devices into which the arrays of this invention may be incorporated include, for example, a sequencing machine or genetic analysis machine.

The single polynucleotides immobilised onto the surface of a solid support should be capable of being resolved by optical means. This means that, within the resolvable area of the particular imaging device used, there must be one or more distinct signals, each representing one polynucleotide. Typically, the polynucleotides of the array are resolved using a single molecule fluorescence microscope equipped with a sensitive detector, e.g., a charge-coupled device (CCD). Each polynucleotide of the array may be imaged simultaneously or, by scanning the array, a fast sequential analysis can be performed.

The extent of separation between the individual polynucleotides on the array will be determined, in part, by the particular technique used to resolve the individual polynucleotide. Apparatus used to image molecular arrays are known to those skilled in the art. For example, a confocal scanning microscope may be used to scan the surface of the array with a laser to image directly a fluorophore incorporated on the individual polynucleotide by fluorescence. Alternatively, a sensitive 2-D detector, such as a charge-coupled device, can be used to provide a 2-D image representing the individual polynucleotides on the array "Resolving" single polynucleotides on the array with a 2-D detector can be done if, at 100×magnification, adjacent polynucleotides are separated by a distance of approximately at least 250 nm, preferably at lest 300 nm and more preferably at least 350 nm. It will be appreciated that these distances are dependent on magnification, and that other values can be determined accordingly, by one of ordinary skill in the art.

Other techniques such as scanning near-field optical microscopy (SNOM) are available which are capable of greater optical resolution, thereby permitting more dense arrays to be used. For example, using SNOM, adjacent polynucleotides may be separated by a distance of less than 100 nm, e.g., 10 nm. For a description of scanning near-field optical microscopy, see Moyer et al., *Laser Focus World* (1993) 29(10).

An additional technique that may be used is surface-specific total internal reflection fluorescence microscopy (TIRFM); see, for example, Vale et al., *Nature* (1996) 380: 451-453). Using this technique, it is possible to achieve wide-field imaging (up to 100 μm×100 μm) with single molecule sensitivity. This may allow arrays of greater than $10^7$ resolvable polynucleotides per $cm^2$ to be used.

Additionally, the techniques of scanning tunneling microscopy (Binnig et al., *Helvetica Physica Acta* (1982) 55:726-735) and atomic force microscopy (Hansma et al., *Ann. Rev.*

Biophys. Biomol. Struct. (1994) 23:115-139) are suitable for imaging the arrays of the present invention. Other devices which do not rely on microscopy may also be used, provided that they are capable of imaging within discrete areas on a solid support.

Once sequenced, the spatially addressed arrays may be used in a variety of procedures which require the characterisation of individual molecules from heterogeneous populations.

Figure 2:
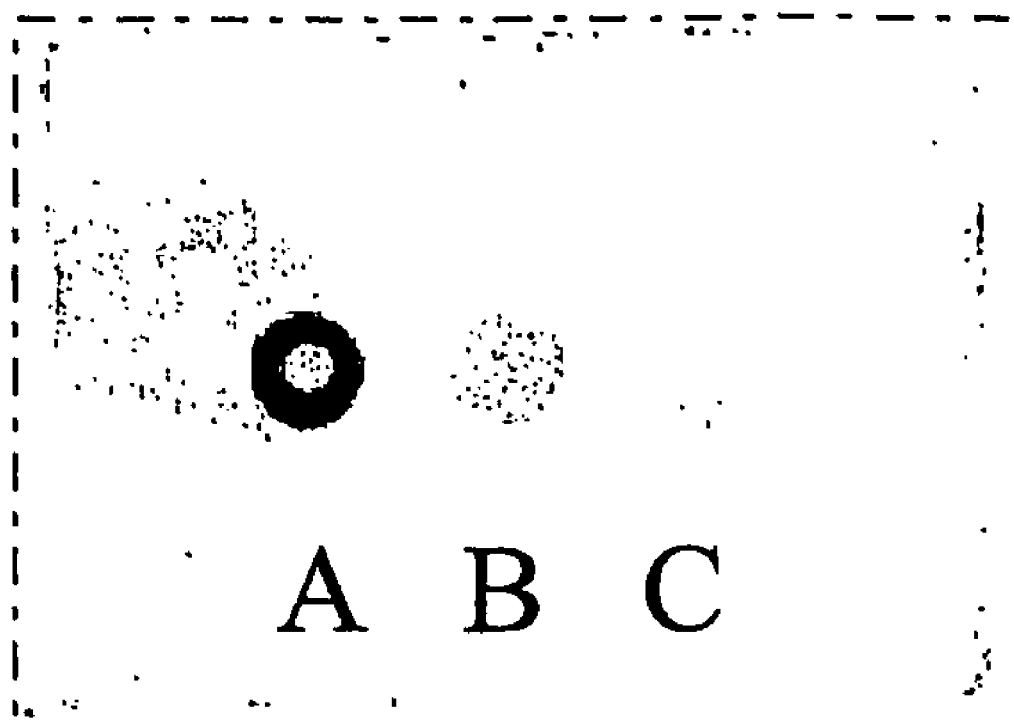
FIG. 2 shows fluor image visualisations of an immobilised branched DNA of the invention (spot A) and two other DNAs (spot B and C).
Figure 3:
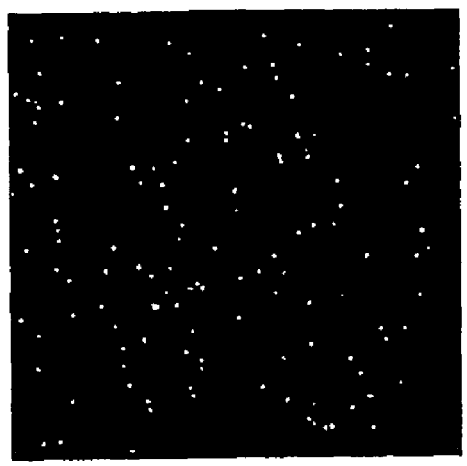
FIG. 3 shows total internal reflection microscopic images of a DNA of the invention (D) and a further DNA (spot E).
Figure 3:
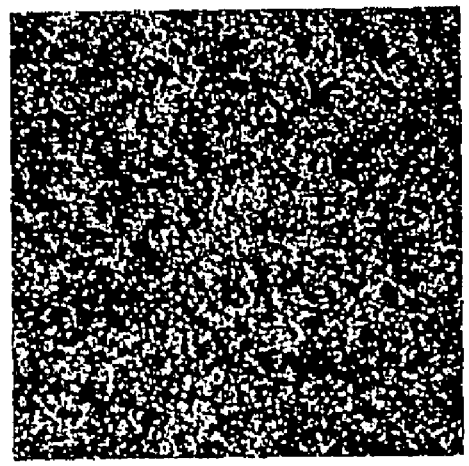

The following examples, with reference to FIGS. 2 and 3, illustrate the invention but in no way are intended to restrict its scope.

EXAMPLE 1

Use of Thiophosphate as the Sulfur-based Nucleophile

Preparation of the Slides

Glass slides were transferred into racks and washed with agitation and without drying between stages as follows: overnight in detergent (Decon 90), rinse (water), overnight in 1 M NaOH, rinse (water), 15 minutes in 0.1 M HCl, rinse (water), and then stored in ethanol.

Slide Functionalization

A solution of 0.2% total silane, as a mixture of tetraethoxysilane and triethoxysilylpropyl (bromoacetamide) at 100:1 in 95% aqueous ethanol (adjusted to approximately pH 4.5 with 5% $H_2SO_4$) was prepared. Hydrolysis of the silanes and silanol formation took place during a 5 minute preincubation step with sonication. The cleaned slides were immersed in the silane solution for 6 minutes before they were removed and washed with isopropanol. The slides were then dried under an argon stream and cured in an oven at 120° C. for 90 minutes.

DNA Immobilization

Bromoacetylated slides were used as support for DNA immobilization. Oligonucleotides with terminal thiophosphate modifications were covalently attached from solution (0.1 M potassium phosphate buffer pH 7.0) for 15 minutes a ambient temperature. The terminal thiophosphate modification was attached during oligonucleotide synthesis through an abasic nucleoside phosphoramidite and used as supplied (Oswel). Backbone phosphorothioate DNA was synthesized using phosphoramidite chemistry and used as supplied (Oswel). Control DNAx with no thiophosphate modification were modified with a C6 amine group.

Post-immobilization, the slides were rigorously washed by vortexing (20 seconds each step) in MiliQ grade water, 10 mM Tris pH 8.0, 10 mM EDTA solution at 95° C., MilliQ grade water before drying under argon.

Three cy3 fluorescently labelled sample DNAs were applied from 0.1 M potassium phosphate buffer pH 7.0 which were visualised using a fluor imager, represented in FIG. 1, in which:

Spot A corresponds to a branched hairpin DNA with terminal thiophosphate;

Spot B corresponds to a hairpin DNA with four phosphorothioate backbone modifications; and Spot C corresponds to a single amine modification (negative control).

FIG. 2 demonstrates the comparative coupling efficiencies of the three DNAs. Under the reaction conditions described there is an increased signal from terminal (branched) thiophosphate (A) over backbone phosphorothioate (B) on a bromoacetylated slide. This is due to either less steric hindrance or increased reactivity of the thiophosphate moiety over the phosphorothioate moiety buried in the backbone of the DNA. Under these application conditions there is minimal non-specific association of the control (amine-terminated; C) DNA with the substrate.

Diluting the proportion of reactive silane to 1 part bromoacetamide in 10000 tetraethoxy gave slides suitable for single molecule analysis. FIG. 3 shows a total internal reflection microscopy image of single molecule of two different DNA species. Images D and E both show images of 5 nM Cy3-prelabeled DNA coupled for 15 minutes at room temperature respectively. Image D contains hydroxyl-terminating DNA and image E shows thiophosphate-terminating DNA. The larger number of spots in image E shows both that the terminal thiophosphate DNA couples more efficiently than the control (image E) and that the coupled molecules are resolvable at the single molecule level.

EXAMPLE 2

Use of Thiol as Sulfur-based Nucleophile

Slides are prepared and functionalised as described in Example 1. Thereafter oligonucleotides with terminal thiol modification are covalently attached to the slides under conditions as described in Example 1.

The oligonucleotides with terminal thiol modification are prepared by incorporation into the hairpin of the following nucleotides (A) and (B), which are exemplary of those which contain protected terminal thiol functionality:

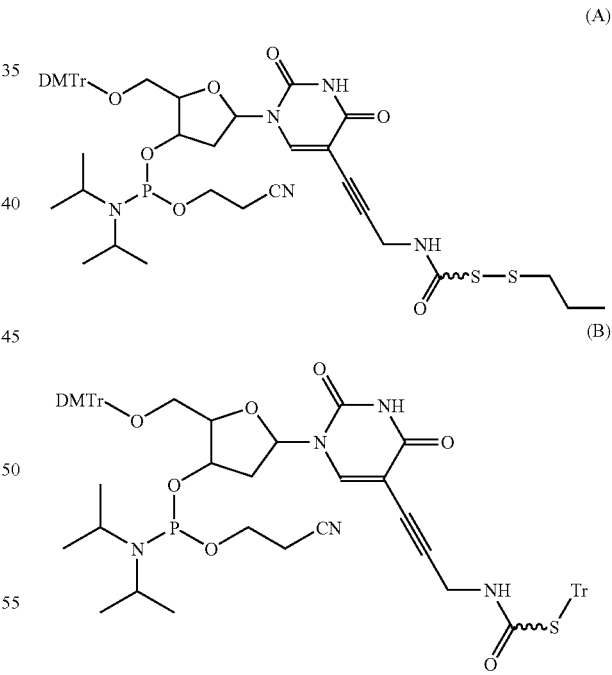

The nucleotides (A) and (B) above can be used to prepare hairpin DNA containing an internal thiol. The abasic version can also be used. The lines~in each of structures (A) and (B) indicate either a direct bond between the sulfur atom and the carbonyl group or a linking moiety connecting the sulfur atom and the carbonyl group.

During oligonucleotide synthesis, nucleotides (A) and (B) can be used as conventional monomers to incorporate a protected thiol functionality. After synthesis, the thiol protecting group in nucleotides (A) is removed by dithiothreitol (DTT) to give the free thiol in solution); similarly the trityl group in (B) is removed by silver nitrate. Examples of (A) and (B) can then be used in the same conditions as the thiophosphate hairpin described in Example 1 to couple to the bromoacetamide surface.

Where the lines~in each of structures (A) and (B) indicate a direct bond, compounds (II) and (III) respectively are defined and their syntheses are now described:

Part A: Preparation of Precursor Acids (IV) and (V):

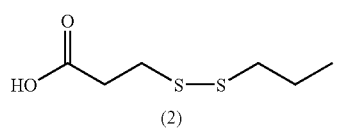

(IV)
(2)

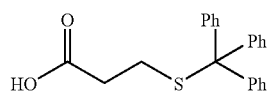

(V)

Propanethiol (3 mmol, 0.23 g) was added dropwise to a solution of aldrithiol (6 mmol, 1.32 g) in 15 mL methanol (MeOH). After 1.5 h the reaction had gone to completion and the solvent was evaporated. The crude product (VI)

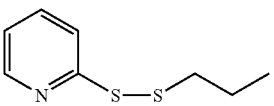

(VI)

was-purified by chromatography on silica with ethyl acetate: petroleum ether (1:4). MW 185.3

Mercaptopropionic acid (2.06 mmol, 0.22 g) was added to a solution of (VI) (3.27 mmol, 0.60 g) in 20 mL MeOH. The mixture was stirred for 2.5 h and the solvent was removed under reduced pressure. The crude acid (IV) was purified by chromatography on silica with $CHCl_3$:MeOH:acetic acid(AcOH)(15:1:0.5) as the solvent mixture. MW 180.3

Mercaptopropionic acid (2.06 mmol, 0.22 g) was added to a solution of trityl chloride (3.09 mmol, 0.86 g) in tetrahydrofuran (THF)/triethylamine (99:1, 50 mL). The mixture was stirred for 6 h and the solvent was removed under reduced pressure. The crude acid (V) was purified by chromatography on silica with $CHCl_3$: MeOH (19:1) as the solvent mixture. MW 348.5.

Part B: Preparation of Nucleotides (II) and (III):

Preparation of 5-[3- (2,2,2-trifluoroacetamido)-prop-1-ynyl]-2'-deoxyuridine (VII)

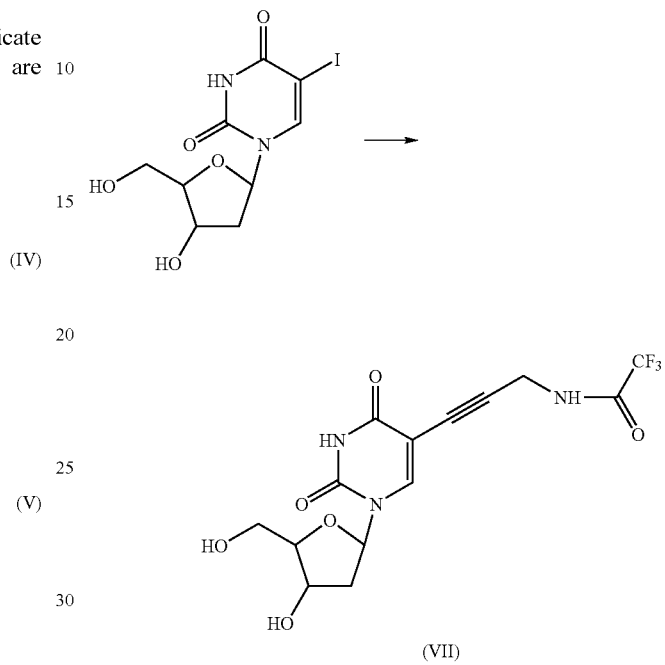

(VII)

To a solution of 5-iodo-2'-deoxyuridine (1.05 g, 2.96 mmol) and CuI (114 mg, 0.60 mmol) in dry dimethylformamide (DMF) (21 ml) was added triethylamine (0.9 ml). After stirring for 5 min trifluoro-N-prop-2-ynyl-acetamide (1.35 g, 9.0 mmol) and $Pd(PPh_3)_4$ (330 mg, 0.29 mmol) were added to the mixture and the reaction was stirred at room temperature in the dark for 16 h. MeOH (40 ml) and bicarbonate dowex added to the reaction mixture and stirred for 45 min. The mixture was filtered and the filtrate washed with MeOH and the solvent was removed under vacuum. The crude mixture (VII) was purified by chromatography on silica ethyl acetate (EtOAc) to EtOAc:MeOH 95:5). MW 377.3

Preparation of (VIIIa) and (VIIIb)

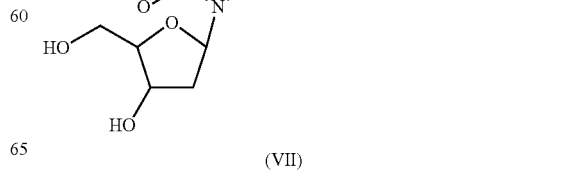

(VII)

-continued

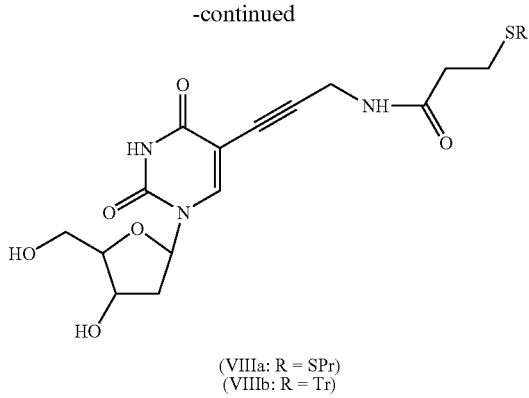

(VIIIa: R = SPr)
(VIIIb: R = Tr)

The trifluoroacetamidyl group was removed using aqueous ammonia immediately prior to use. The ammonia solution was removed and the material was re-suspended in DMF. The appropriate acid ((IV) or (V) prepared in Part A) was suspended in DMF with one equivalent of 1,3-dicyclohexylcarbodiimide (DCC) and two equivalents of N-hydroxy succinimide. The activation was stirred at room temperature for 1 h and the amino nucleoside added (1 equivalent). The reaction was stirred for 12 h, the solvents removed and the material purified by silica chromatography. In both cases the material was eluted with $CHCl_3$/MeOH 19:1. MW 611.7 (VIIIb); 443.5 (VIIIa).

Preparation of (IXa) and (IXb)

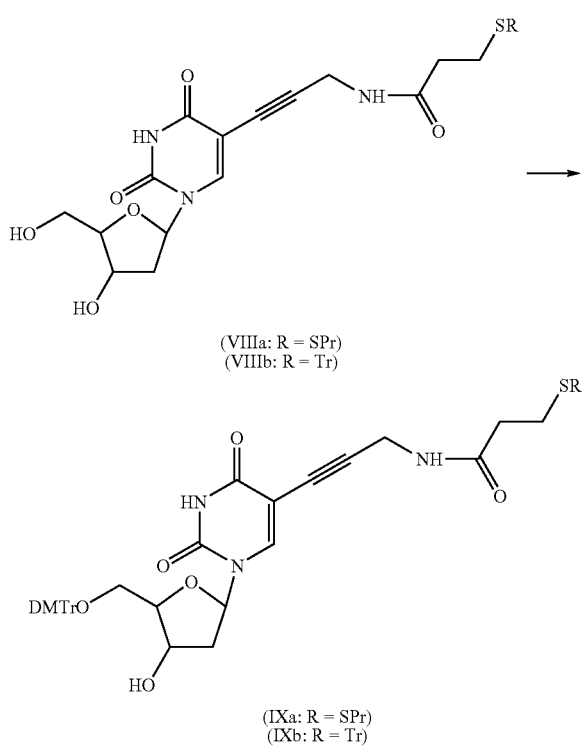

(VIIIa: R = SPr)
(VIIIb: R = Tr)

(IXa: R = SPr)
(IXb: R = Tr)

R = SPr or Tr

The nucleoside (VIIIa) or (VIIIb) (1 mmol) was dissolved in pyridine (20 mL). Dimethoxytrityl chloride (1.2 mmol, 0.41 g) was added and the reaction was stirred at room temperature for 4 h. The solvent was removed and the material purified by silica chromatography. (IXa) or (IXb) was eluted with $CHCl_3$/MeOH 49:1. MW 914.1 (IXb); 745.9 (IXa).

Preparation of (II) and (III):

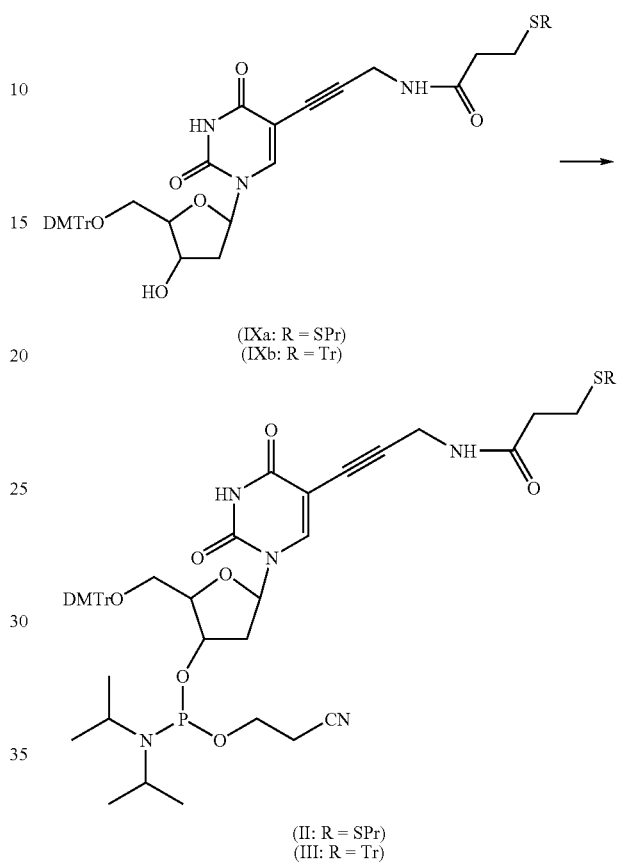

(IXa: R = SPr)
(IXb: R = Tr)

(II: R = SPr)
(III: R = Tr)

The protected nucleoside ((IXa) or (IXb)) (0.5 mmol) and diisopropylammonium tetrazolide (0.25 mmol, 0.043 g) were dissolved in dry dichloromethane (5 mL). Bis(diisopropylamino)2-cyanoethoxyphosphine (0.55 mmol, 0.166 g) was added and the reaction stirred under nitrogen for 1 h. The reaction was diluted with dichloromethane and extracted with sodium bicarbonate and brine. The dried organic layer was concentrated and purified by silica chromatography. The material ((II) or (III)) was eluted with $CHCl_3$/MeOH 49:1 and stored dry in a desiccator until use in DNA synthesis.

During oligonucleotide synthesis, nucleotides (II) or (III) can be used as conventional monomers to incorporate a protected thiol functionality. All other protecting groups were removed from the oligonucleotides during purification, the thiol protecting group was removed immediately prior to use. The thiol protecting group in (II) is removed by DTT and in (III) by silver nitrate to give the free thiol. The oligonucleotide was purified by reverse phase HPLC and stored under nitrogen until used.

The invention claimed is:

1. A hairpin polynucleotide, having a loop and a stem region, characterised in that the hairpin polynucleotide comprises a sulfur-based nucleophile, wherein the sulfur-based nucleophile is a moiety of the formula (I):

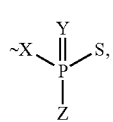

(I)

wherein ~ denotes a linker connecting the sulfur-based nucleophile to the remainder of the polynucleotide; X represents an oxygen atom, a sulfur atom or a group NR, in which R is hydrogen or an optionally substituted $C_{1-10}$ alkyl; Y represents an oxygen or a sulfur atom; and Z represents an oxygen atom, a sulfur atom or an optionally substituted $C_{1-10}$ alkyl group, and wherein the sulfur-based nucleophile is attached to the base of an internal nucleotide or to the 1'-carbon atom of an abasic internal nucleotide in the hairpin through a linker to enable binding to a solid support.

2. The hairpin polynucleotide as claimed in claim 1 wherein the internal nucleotide is present in the loop of the hairpin.

3. The hairpin polynucleotide as claimed in claim 1 wherein X is oxygen, sulfur, or NH.

4. The hairpin polynucleotide as claimed in claim 1 wherein Y is oxygen.

5. The hairpin polynucleotide as claimed in claim 1 wherein Z is an oxygen or sulfur atom or a methyl group.

6. The hairpin polynucleotide as claimed in claim 1 wherein the sulfur-based nucleophile is a thiophosphate moiety.

7. The hairpin polynucleotide as claimed in claim 1 comprising a DNA or an RNA.

8. A hairpin polynucleotide as claimed in claim 1 wherein said linker is selected from the group comprising polyethylene glycol of formula $-(CH_2-CH_2-O)_m$ (wherein m is an integer of from about 1 to about 600), dextrose, peptides, nucleic acids or modified or unmodified chain of formula $-(CH_2)_n$ (wherein n is an integer of from about 1 to about 1,500).

9. A hairpin polynucleotide as claimed in claim 8 wherein the linker comprises a modified chain of formula $-(CH_2)_n$ wherein n is less than 100 and the modifications comprise the replacement of one or more than one $CH_2$ units for functional groups selected from the group comprising ketones, esters, amines, amides, ethers, thioethers, sulfoxides, sulfones, alkene, alkyne, aromatic or heteroaromatic moieties or cyclic aliphatic moieties.

10. The hairpin polynucleotide as claimed in claim 9 wherein the modified chain comprises one or more amide bonds and one or more carbon-carbon triple bonds.

11. The hairpin polynucleotide as claimed in claim 8 wherein the linker comprises a propargylamino unit.

12. The hairpin polynucleotide as claimed in claim 1 comprising a first target polynucleotide attached to the 5' end of the hairpin.

13. The hairpin polynucleotide as claimed in claim 12 wherein said first target polynucleotide is genomic DNA.

14. The hairpin polynucleotide as claimed in claim 12 wherein said first target polynucleotide is human genomic DNA.

15. The hairpin polynucleotide as claimed in claim 1 comprising a primer attached to the 3' end of the hairpin.

16. The hairpin polynucleotide as claimed in claim 1 wherein the stem comprises a 5 to 25 base pair double-stranded region.

17. The hairpin polynucleotide as claimed in claim 1 wherein the loop comprises 2 or more non-hybridised nucleotides.

18. The hairpin polynucleotide as claimed in claim 1 formed from 2 or more separate polynucleotides with complementary regions and a loop which comprises a non-nucleotidic connecting moiety.

19. The hairpin polynucleotide as claimed in claim 18 wherein said linker moiety comprises PEG.

20. A method of making a hairpin polynucleotide, as defined in claim 1, comprising attaching the sulfur-based nucleophile to said internal nucleotide before, after or during formation of the hairpin polynucleotide.

21. An array of hairpin polynucleotides as defined in claim 1 immobilised on a surface of a solid support.

22. The array as claimed in claim 21 which is a single molecular array.

23. The array as claimed in claim 21 wherein said solid support comprises glass, ceramics, glass silicon or plastics.

24. The array as claimed in claim 21 wherein said solid is a glass slide.

25. The array as claimed in claim 21 wherein the hairpin polynucleotides are immobilised by covalent bonding.

26. The array as claimed in claim 25 wherein said covalent bonding is formed between the sulfur-based nucleophile and an electrophilic group displayed on the surface of the solid support.

27. The array as claimed in claim 26 wherein said electrophilic group is attached to a silicon atom.

28. The array as claimed in claim 27 wherein said surface is modified so that it in part comprises a silane of formula $R_n SiX_{(4-n)}$ (where R is an inert moiety that is displayed on the surface of the solid support, n is an integer of from 1 to 4 and X is or comprises a reactive leaving group).

29. The array as claimed in claim 26 wherein the electrophilic group is formed from bromoacetamide functionality.

30. A method of making an array as defined in claim 21 comprising the steps of:
(i) preparing a plurality of said hairpin polynucleotides; and
(ii) immobilising said hairpin polynucleotides to a surface of a solid support so as to form said array.

31. The method of making an array of hairpin polynucleotides as claimed in claim 30 comprising an additional subsequent step of ligating a second target polynucleotide to each hairpin polynucleotide after they have been immobilised to the surface of the solid support.

32. The method of making an array as claimed in claim 31 wherein said second target polynucleotide is genomic DNA.

33. The method of making an array as claimed in claim 31 wherein said second target polynucleotide is human genomic DNA.

34. The method of making an array as claimed in claim 30 wherein either or both of said first and second target nucleotides is or are attached to the hairpin polynucleotides by ligating one strand of the target nucleotide in the form of a double-stranded DNA to the hairpin polynucleotide and removing the other strand after the ligation.

35. A device comprising an array as defined in claim 21.

36. An analytical procedure to determine the sequence of the first target polynucleotide, comprising interrogating the hairpin polynucleotides of the device of claim 35.

* * * * *